United States Patent
Bredenbreuker et al.

(10) Patent No.: US 10,119,550 B2
(45) Date of Patent: Nov. 6, 2018

(54) PUMP HOUSING WITH AN INTERIOR FOR ACCOMMODATING A PUMP ROTOR

(71) Applicant: ECP ENTWICKLUNGSGESELLSCHAFT MBH, Berlin (DE)

(72) Inventors: Lars Bredenbreuker, Berlin (DE); Joerg Schumacher, Teltow (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 521 days.

(21) Appl. No.: 13/261,899

(22) PCT Filed: Dec. 21, 2012

(86) PCT No.: PCT/EP2012/076635
§ 371 (c)(1),
(2) Date: May 19, 2014

(87) PCT Pub. No.: WO2013/093001
PCT Pub. Date: Jun. 27, 2013

(65) Prior Publication Data
US 2014/0255176 A1 Sep. 11, 2014

Related U.S. Application Data (60) Provisional application No. 61/579,122, filed on Dec. 22, 2011.

(30) Foreign Application Priority Data

Dec. 22, 2011 (EP) .................................. 11075271

(51) Int. Cl.
*F04D 29/18* (2006.01)
*F04D 29/52* (2006.01)
(Continued)

(52) U.S. Cl.
CPC ........... *F04D 29/18* (2013.01); *A61M 1/1024* (2014.02); *F04D 15/0005* (2013.01);
(Continued)

(58) Field of Classification Search
CPC .... F04D 15/0004; F04D 29/026; F04D 29/18; F04D 29/181; F04D 29/247;
(Continued)

(56) References Cited

U.S. PATENT DOCUMENTS 6,533,716 B1 3/2003 Schmitz-Rode et al.
7,027,875 B2 4/2006 Siess et al.
(Continued)

FOREIGN PATENT DOCUMENTS

DE 29804046 U1 4/1998
DE 10059714 C1 5/2002
(Continued)

*Primary Examiner* — Audrey K Bradley
(74) *Attorney, Agent, or Firm* — White & Case LLP (57) ABSTRACT

In a pump housing having an interior for accommodating a pump rotor, which may be transferred from a radially compressed state into a radially expanded state, and comprises a housing skin revolving in circumferential direction, as well as at least one reinforcement element, a stretch-resistant element revolving in circumferential direction is provided, which is stretched less than 5% in the expanded state as opposed to the force-free state in circumferential direction, and which limits any further expansion of the pump housing in radial direction.

20 Claims, 6 Drawing Sheets

(51) Int. Cl.
*A61M 1/10* (2006.01)
*A61M 1/12* (2006.01)
*F04D 15/00* (2006.01)
*F04D 29/02* (2006.01)
*F04D 29/24* (2006.01)

(52) U.S. Cl.
CPC ......... *F04D 29/026* (2013.01); *F04D 29/181* (2013.01); *F04D 29/247* (2013.01); *F04D 29/528* (2013.01); *A61M 1/101* (2013.01); *A61M 1/1034* (2014.02); *A61M 1/1098* (2014.02); *A61M 1/122* (2014.02); *A61M 1/125* (2014.02); *F05D 2300/174* (2013.01); *F05D 2300/505* (2013.01); *F05D 2300/603* (2013.01); *F05D 2300/6034* (2013.01)

(58) Field of Classification Search
CPC ............. F04D 29/528; F05D 2300/174; F05D 2300/505; F05D 2300/603; F05D 2900/6034; A61M 1/101; A61M 1/1024
See application file for complete search history.

(56) References Cited

U.S. PATENT DOCUMENTS

| | | | |
|---|---|---|---|
| 7,393,181 | B2 | 7/2008 | McBride et al. |
| 7,841,976 | B2 | 11/2010 | McBride et al. |
| 7,927,068 | B2 | 4/2011 | McBride et al. |
| 8,376,707 | B2 | 2/2013 | McBride et al. |
| 2011/0071338 | A1 | 3/2011 | McBride et al. |
| 2013/0041202 | A1 | 2/2013 | Toellner |
| 2013/0066140 | A1 | 3/2013 | McBride et al. |
| 2013/0129503 | A1 | 5/2013 | McBride et al. |

FOREIGN PATENT DOCUMENTS

| | | |
|---|---|---|
| EP | 1201932 A2 | 5/2002 |
| EP | 2047872 B1 | 9/2010 |
| EP | 2347778 A1 | 7/2011 |
| WO | 03/103745 A2 | 12/2003 |

PUMP HOUSING WITH AN INTERIOR FOR ACCOMMODATING A PUMP ROTOR

BACKGROUND OF THE INVENTION

The invention resides in the mechanical field, and more particularly in the medical engineering field. It relates to pumps being equipped with pump rotors and having a pump housing, the interior of which accommodates the pump rotor. In particular in the medical engineering field, however, generally also in any other technical fields of application, pumps are known, which may be radially compressed in that both the rotor and the pump housing may be deformed in order to reduce the diameter, and which are expandable at the site after transport, in order to adjust to the measurements required for an optimized function. Further, in particular in the medical engineering field, such pumps are known, which may be compressed such that the same may be inserted into a blood vessel into the body of a patient, and may be expanded there, in order to support or independently enable the blood transport via the operation of the pump.

In order to ensure a reliable collapsibility and expandability, a plurality of technical problems must be solved.

For example, U.S. Pat. No. 7,393,181 B2 describes a collapsible pump rotor, in which conveyor vanes are disposed in rows on a hub, and may be retractable on the same.

A pump rotor is known from U.S. Pat. No. 7,841,976 B2, which may be inserted into the expandable part of a cannula, in order to be operated there after the respective cannula part has expanded. For this purpose the rotor is driven via a shaft extending through the cannula. The pump formed in this manner may be advanced through a blood vessel all the way into a heart chamber, and operated at that location.

U.S. Pat. No. 7,927,068 B2 also describes a pump having a rotor, which has a hub and retractable and tiltable conveyor vanes. The conveyor vanes are pushed into the position suitable for the pump operation during the operation of the rotation by means of the fluid counter pressure created.

An intravascular pump having a collapsible and expandable housing is known from DE 100 59 714 01, which has a mesh. This housing may accommodate a rotor, and may be inserted into a blood vessel by means of an insertion lock.

The prior art state above generally deals with the problems of compressing a pump having a rotor and a pump housing radially sufficient so that the same may, for example, be inserted into a blood vessel of a patient, and may be expanded after insertion. At a later time the respective pump should also be collapsible again in order to be able to be removed. In the compressing and expansion process both the rotor and the housing are commonly deformed correspondingly. A special challenge is found in the requirement of minimizing the pump gap, i.e. the intermediate space between the rotor, more specifically the radial external ends of the conveyor vanes, and the internal housing wall of the pump housing during operation, in order to optimize the pump operation, in particular the effectiveness and the compressing of the pump. The pump gap must be very small and, in particular, must be held as constant as possible in order to prevent any overflow at the radial external ends of the conveyor elements of a rotor, on the other hand the conveyor elements or other elements of the rotor should not contact the interior wall of the pump housing, if at all possible, in order not to generate any unnecessary friction losses or abrasion wear at the commonly high rotational speeds of more than 10,000 rotations per minute.

BRIEF SUMMARY OF THE INVENTION

Against this background of prior art the object of the present invention is therefore to create a pump housing and a pump of the type mentioned above, which allow an adjustment of the pump gap that is as accurate end reproducible as possible.

Accordingly, the pump housing has a housing skin and at least one reinforcement element, wherein in the fully expanded state of the housing the housing skin is tightened in circumferential direction by means of the expansion of the reinforcement element, and wherein at least one element that is circumferential in circumferential direction in a stretch-resistant manner, is provided, which is tightened in the expanded state as opposed to the power-free state in circumferential direction less than 5%, in particular less than 1%, and which limits the further expansion of the pump housing.

The housing skin may consist of an easily deformable, flexible, in particular pliable plastic material, and may contain, for example, a polymer. The housing skin may be simply disposed about the reinforcement element, or may be connected to the same by means of common joining techniques, such as gluing or welding. The reinforcement element may also be integrated in the housing skin by means of casting.

Usually, the reinforcement element is configured and disposed such that it supports the housing skin radially from the interior. This is also possible in case of integration of the reinforcement element, for example via casting, into the housing skin.

With an expansion of the pump housing from a compressed state the reinforcement element or a group of reinforcement elements deform and tighten the housing skin, in that they exert a force which acts radially toward the exterior onto the same. The hydrodynamic, and in particular hemodynamic properties of the pump housing are particularly improved, if the housing skin is tightened, in particular tightened in a crease-free manner, and the interior wall of the pump housing limiting the interior for accommodating the pump rotor is as smooth as possible.

However, should this not lead to the fact that variable stretching forces are created by means of the forces acting upon the housing skin, depending on the size of the forces acting by means of the reinforcement elements such that the measurements of the interior of the housing vary. For this purpose the invention provides a stretch-resistant element revolving in circumferential direction, which may not be stretched in any essential manner by means of the forces acting radially toward the exterior of the reinforcement element(s). The stretch-resistance element is advantageously disposed in the axial section of the pump housing accommodating the pump rotor. For this purpose the stretch-resistant element may also cover the entire axial length of the pump rotor.

The stretchable element may also be a flexible film, which is, for example, substantially more stretch-resistant than the housing skin, and may radially surround the same.

The stretch-resistant film may also surround merely the reinforcement elements, may be radially surrounded itself by the housing skin, or may replace the housing skin.

The pump housing in turn advantageously comprises an axial section, in which the interior is formed essentially cylindrical. This cylindrically formed axial interior area may accommodate, for example, the pump rotor.

Such cylindrical form should also comprise approximately circular cylindrical shapes formed as polygonal prisms, or as polyhedrons, each inscribed to a circular cylinder, and which are created by the housing skin supports by means of bracers. The individual limiting surfaces, of which the forms consist, may be, for example, diamond-shaped.

The pump housing, or the interior thereof, respectively, may axially protrude more or less beyond the length of the pump rotor relative to the axial section provided for accommodating the pump rotor, for example, by at least 2 cm, in particular at least 5 cm, further in particular at least 8 cm. The area of the pump housing extending beyond the length of the axial section provided for accommodating the pump rotor may be positioned distally from the pump rotor, i.e. toward the end of the pump housing, an which the same has the suction side thereof with a suction opening. An ejection opening is provided for the fluid to be transported at the proximal end of the pump housing. However, the rotor may also at least partially protrude beyond the structure enclosed by a housing skin.

The suction opening of the pump housing may be, for example, an opening at the front side, which is advantageously covered by a suction cage. The suction cage may have the shape of, for example, a ball calotte, or may also initially provide an expansion via the diameter of the pump housing in a balloon shape, which is terminated toward the distal end by means of a calotte, or also by means of a point equipped with a pigtail. The suction cage may be formed by means of continuous reinforcement elements of the pump housing.

The pump housing may be cylindrically formed up to the suction end thereof, and may advantageously have a funnel-shaped expansion at the end on the suction side, from which the reinforcement elements exit and form a balloon-shaped expanded suction cage.

On the ejection side, or at the end at the ejection side, the pump housing advantageously also has an opening at the front. There, reinforcement elements can also exit from the wall of the pump housing and be guided to the central symmetry axis of the pump housing, wherein the same retain and center a catheter extending coaxially toward the pump housing with a smaller diameter than that of the pump housing, and may accommodate, for example, a drive shaft for a pump rotor.

The shape and size, as well as the pre-treatment of the reinforcement element(s) are advantageously selected such that the elastic forces of the reinforcement element(s) going beyond the actual radial expansion of the housing, are so large the excess forces directed radially toward the exterior are greater than 1 N, preferably 4 N. This means that even a radial force of the reinforcement elements that is reduced by the excess forces would still result in a full expansion of the housing.

In this manner it is ensured that the housing is not deformable, in particular is not collapsible with regard to the diameter of the interior, even by a certain limited radial pressure from the exterior (a maximum of the same size as the excess forces). In order to compress the pump housing, forces are necessary which exceed forces of the reinforcement elements that act at least radially from the inside.

In this manner it is ensured, in particular in case of a position of the pump housing in the aortic valve that with the closure of the valve the pump housing will not be compress, thereby jamming the rotor, or will not be decelerated upon contact at the pump housing. Such contact would result in the loss of pump performance, and also to the creation of friction and hemolysis, i.e. damage of blood due to acting shear and grinding forces.

The reinforcement element(s) may be composed, for example, of elastically collapsible bracers from metal or plastic, which are released for the expansion of the pump housing, and are elastically deformed. A reinforcement element may, for example, also be formed as an annular revolving element, such as an open circular ring, which revolves about the circumference of the pump housing, and may as a whole be deformed between a spiral-like wound, compressed state and an expanded state, in which it is expanded into a diameter enlarged by an annular ring or a winding.

It is also conceivable that the reinforcement element(s) form a vault, or an arch, respectively, expanding by means of pivoting individual elements against each other. In the forming of such a vault, or an arch, it may also be provided to engage the same into a self-stabilizing position in the expanded state.

An advantageous embodiment of the invention provides that the reinforcement element(s) resist forces directed toward the interior of at least 1 N, preferably 4 N, in the expanded state of the arch or vault formed by the housing, without compressing.

If the forces directed radially toward the interior significantly exceed this threshold, the vault or the arch caves in such that the pump housing reduces the exterior dimensions thereby by means of compression, and may again expand after the forces directed toward the interior are discontinued. The collapse of the arch or vault may be reversible or irreversible.

Another advantageous embodiment of the invention provides that the stretch-resistant element is formed by means of a pliable film, in particular by means of the housing skin.

It may also be provided that the stretch-resistant element is formed by means of a ring revolving in circumferential direction of the housing, surrounding the reinforcement element at least in sections. In particular, the stretch-resistant element may surround the reinforcement element(s) in that area, in which the pump rotor is accommodated.

Advantageously, it may also be provided that the stretch-resistant element is disposed on the radially external side of the housing skin.

For the stabilization of the stretch-resistant element, in particular of also of the entire housing skin, it may also be advantageously provided that the stretch-resistant element has stretch-resistant fibers extending in circumferential direction, in particular glass fibers or carbon fibers. Other fibers or reinforcement elements for improving the stretch resistance are also conceivable.

A particular embodiment of the reinforcement elements provides that the same form a surface-like, two-dimensional grate which is bent into the shape of a tube. The individual grate elements may advantageously be displaced against each other, and/or pivoted, or also elastically deformed, or bent, such that a deformation of the tube-shaped structure is easily possible. The reinforcement elements may revolve in the circumferential direction of the pump housing, for example, in the manner of a saw tooth, or in a meandering manner.

It may also advantageously be provided that multiple reinforcement elements being pivotable against each other form the shape of a tube in a first pivoting state, and are compressed radially as opposed to the tube shape in a second pivoting state. For this purpose the reinforcement element can be connected with each other, for example, at individual points, and form joints, wherein the joint function may be realized by means of hinge-type devices, but also by means of elastic deformation.

It may also be advantageously provided that the housing interior tapers in axial direction in a reducing manner, in particular in a conical manner. This opens up the possibility to axially displace the rotor to be incorporated in the housing interior far enough such that the housing gap, i.e. the intermediate space between the interior wall of the housing interior and the radially most externally positioned ends of the rotor, in particular of the feed elements of the rotor, are optimized, for example, minimized. For this purpose the cone angle of the housing interior may advantageously be between 0.5° and 5°, in particular between 0.5° and 2°.

In this regard, the exterior contour of the pump rotor may also advantageously taper conically as the housing interior, furthermore advantageously having substantially the same cone angle. During the operation of the rotor the same may then be axially displaced in the housing interior far enough until optimal pump performance is reached. This may be determined, for example, by means of a flow measurement, and/or in connection with a power reading of the drive motor of the pump rotor. For example, the rotor may be moved far enough until a marked deceleration occurs, which speaks in favor of the rotor contacting the interior wall of the housing interior, and the rotor may be returned about a defined axial distance, and fixed in this axial position.

However, the housing interior may also have a slightly convex (ball-shaped), or concave shape. This is of particular advantage, if the rotor has different exterior contours due to the deformation in the current field at different operational states (e.g. speed). Depending on the base form of the rotor, a housing form is necessary in this case, which meets the respective requirements of all operational states.

Regardless whether a conical rotor or a rotor having a cylindrical contour, and a housing interior in a conically tapering, or strictly cylindrical shape, are used, the pump gap should be between 0.01 mm and 1 mm, in particular between 0.01 mm and 0.3 mm, further advantageously between 0.03 mm and 0.15 mm. For this purpose the pump gap denotes the minimum distance between a most radially external end of a part of the rotor and the interior wall of the housing interior, which occurs with the rotation of the rotor. In any case, it should be advantageously ensured that the rotor will not contact the pump housing during normal operation.

In order to achieve an optimized compressibility and expandability of the pump housing, it may be advantageously provided that the reinforcement element(s) consist of a super-elastic material, in particular a super-elastic alloy, particularly nitinol. Such materials may be compressed very strongly without any problems, and may also be configured as memory materials, in particular memory alloys, which assume a previously selected form, for example, with the occurrence of a certain temperature change, or of a target temperature.

In addition to a pump housing of the type described above, the invention also relates to a blood pump with a respective pump housing, and with a rotor.

The rotor may consist of, for example, plastic, in particular polyurethane, and advantageously also of foam. It has one or more conveyor elements conveying a liquid in radial and/or axial direction with regard to the rotational axis. The conveyor elements may be embodied as paddles, or as a single continuous paddle, wherein the single paddle, or a series of paddles, revolves about a central hub in the manner of a helix.

Also, two conveyor vanes revolving in a screw-type manner may be provided. The conveyor vanes may be embodied in a self-supporting manner without a hub, or they may be attached on a central hub, or may be integral with the same. Advantageously, the hub and the conveyor elements may consist of the same material.

The conveyor elements may be embodied such that they may be folded in for the compression on the hub, and may be folded out for the expansion. In particular, the conveyor elements assume a center position in the powerless and idle state of the rotor, which neither corresponds to the compressed position, nor the expanded position. In order to assume the compressed position, a radial pressure is applied to the conveyor elements from the exterior, in order to abut the same closely to a hub. The radial pressure may be applied, for example, by means of the compression of the housing surrounding the rotor.

If the radial pressure is reduced, the conveyor elements sit up straight for a distance. Another straightening may be effected by means of the fluid counter-pressure at the beginning of the rotation of the rotor in the fluid to be transported.

The conveyor elements are typically embodied such that they have been straightened to a maximum in radial direction during the operation at an optimized speed, in particular at the maximum speed of the pump, and therefore exert the highest possible conveyor effect onto the fluid. In this state of a maximum straightening, the measurements of the interior of the pump housing and of the rotor must be adjusted to each other such that no contact occurs between the two.

It may also be provided that the individual conveyor elements are deformed beyond the state of maximum radial straightening by means of the fluid counter pressure such that they are again compressed radially by the fluid pressure for a distance.

A flow control element, in particular a valve, is advantageously also disposed in the pump housing at an axial distance to the rotor, in particular in the pump interior, in which the rotor is located, which prevents the backflow of the conveyed fluid also during the idle operation of the rotor. The flow control element controls the flow passing the rotor, i.e. for example, the flow through the annular space between a rotor hub and the interior wall of the pump housing.

The control element/valve is located outside of the hub, for example, also at an axial distance to the rotor hub. It comprises, for example, one or more pivotable baffles, which may be moved by the flow itself, in that they are opened by the flow with a flow in the conveying direction, and are automatically closed by the backflow with a flow opposite of the conveyor direction. The baffles themselves may be elastically deformable, and the flow control unit, as well as the rotor, may be radially compressed and expanded.

If a plurality of individual conveyor elements is provided along a hub, they may advantageously be disposed and aligned such that they form the contour of a helical conveyor vane altogether. The individual conveyor elements may then be folded in at the hub, and may be expanded.

The rotor, in particular the hub, however, advantageously both the hub and the conveyor elements, advantageously consists of a foamed polyurethane, a thermoplastic elastomer, a rubber, or a super-elastic material, in particular a super-elastic polymer.

In addition to a pump housing and a blood pump having such a pump housing and a rotor, the invention also relates to a blood pump unit with a pump housing, a rotor, and a catheter connected to the pump housing at one end thereof. The catheter may, for example, be part of a manipulating unit, which allows to at least partially insert the pump housing and the rotor through a blood vessel of a patient into a heart chamber.

In particular, the catheter has a lumen, which is continuous in longitudinal direction, in which a drive shaft for the rotor of the pump is disposed. However, a motor may also be disposed in direct proximity to the pump housing for driving the rotor.

The catheter may also advantageously be directly connected to the pump housing, wherein radial openings for the fluid to be transported may be provided either at the end of the pump housing, and/or at the beginning, or in the extension of the catheter. The catheter advantageously has a substantially small diameter than the interior of the pump housing, and is attached at the end of the pump housing. Advantageously, it is coaxially and concentrically connected to the pump housing. The connection may be carried out, for example, by means of the reinforcement elements of the pump housing, which axially project beyond the pump housing, and may be concentrically bent off radially toward the inside in order to be connected to the catheter at that location. In this manner the extensions of the reinforcement elements/bracers of the pump housing may retain and center the catheter.

BRIEF DESCRIPTION OF THE DRAWINGS

The invention is shown based on an exemplary embodiment in a drawing, described in further detail below. They show:

FIG. 1 a schematic illustration of a blood pump inserted into a heart chamber via a blood vessel, FIG. 2 a blood pump in a heart chamber at a longitudinal section, FIG. 3 a blood pump in a side view, FIG. 4 part of a pump housing with reinforcement elements, FIG. 5 a side view of a pump housing with reinforcement elements, FIG. 6 reinforcement elements for a pump housing in an expanded form, FIG. 7 the reinforcement elements of FIG. 6 in a compressed form, FIG. 8 a longitudinal section across part of a pump housing with a rotor, wherein the pump housing is embodied conically, FIG. 9 part of a longitudinal section of a pump housing with a rotor, wherein the housing interior is embodied cylindrically, FIG. 10 a schematic longitudinal section across a blood pump, FIG. 11 a longitudinal section across part of a pump housing with a reinforcement element, FIG. 12 a longitudinal section across a pump housing with circular reinforcement elements, FIG. 13 a longitudinal section across part of a blood pump with a pump housing, as well as a stretch-resistant element and reinforcement elements, FIG. 14 a longitudinal section across part of a blood pump with a valve downstream of the rotor, FIG. 15 a similar arrangement as in FIG. 14, with a valve upstream of the rotor, FIG. 16 an arrangement, wherein a rotor expels a fluid through a cage via a valve, FIG. 17 an embodiment of a valve in two positions, and FIG. 18 another embodiment of a valve in two positions.

DETAILED DESCRIPTION OF THE INVENTION

Figure 1:
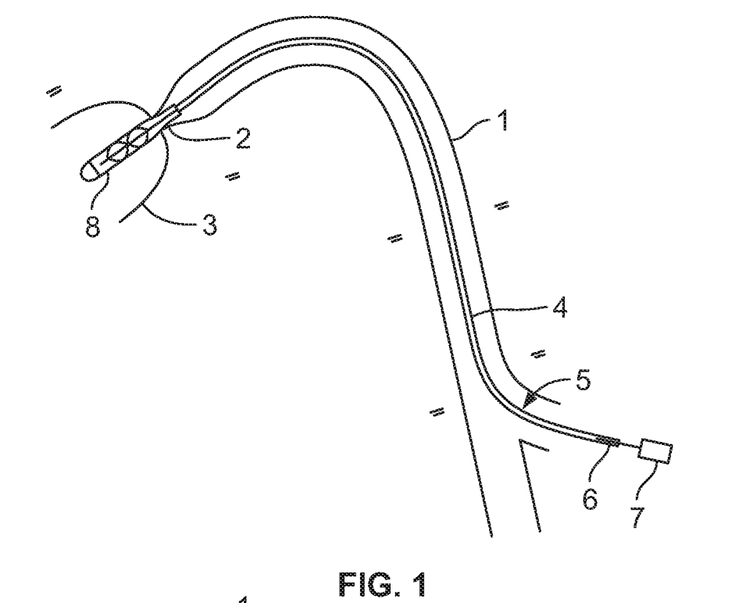

FIG. 1 schematically shows a blood vessel 1 of a human body, which is connected to a heart chamber 3 via a heart valve 2, and into which a catheter 4 is inserted via a lock 5. The catheter 4 has a channel (lumen) in the interior thereof, via which a drive shaft 6 leads from an exterior drive motor 7 into a heart pump 8 inserted into the heart chamber 3. The heart pump 8 may be inserted into the blood vessel, for example, according to the known Seldinger technique, and advanced to the heart chamber through the same.

The heart pump 8 has a rotor inside, which may be driven by a drive shaft 6 at several thousand, typically between 10,000 and 50,000, revolutions per minute, and transports blood in axial direction. The rotor is surrounded by a pump housing having a distal suction opening, via which the blood in the heart chamber 3 may be suctioned off.

Such blood pumps are utilized for the replacement or supplementation of the natural heart function, either temporarily, or also permanently. Especially with the supplemental use of such a heart pump it is of advantage, if the natural activity of the heart remains uninfluenced such that the heart itself may also contribute to the pump function via the heart valve. For this purpose the heart may either provide supplementary pumping action through the pump, or bypassing the same, transport blood to the heart pump through the heart valve.

Figure 2:
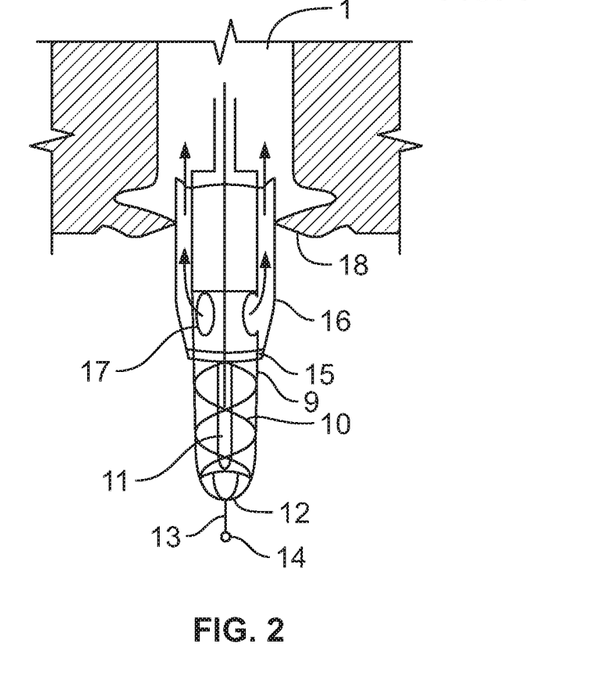

FIG. 2 shows an embodiment of a heart pump having an approximately cylindrical pump housing 9 in an expanded form, containing a rotor 10. For example, the rotor 10 has a conveyor element helically revolving at a hub 11, in the form of a conveyor vane. The space occupied by the rotor during its rotation is cylindrical and matched to the housing interior of the housing 9 as accurately as possible.

The pump housing 9 has a suction cage 12 at the distal end thereof, which is formed by several bracers simultaneously forming the reinforcement elements of the pump housing 9, which are embedded into the material of the pump housing, and axially project beyond the same in a distal direction.

An atraumatic syringe 13 is disposed at the distal end of the suction cage 12, which has the shape of a ball 14 in the example, ensuring that the pump will not damage any vessel walls or heart walls while it is being inserted into the blood vessel and into the heart chamber, and that the suction end with the suction opening 12 of the pump housing 9 will not latch onto the vessel wall during the transport of blood.

A film-like discharge jacket 16 is connected to the pump housing in a fluid tight manner in an axial area 15 of the pump housing. The discharge jacket 16 consists of a flexible, pliable, very thin film covering the discharge openings 17 of the pump housing 9, which are disposed on the side of the jacket, and reaches beyond these a little further in proximal direction of the pump, i.e. in the direction of the lock 5. The heart valve, schematically indicated by reference numeral 18, pushes the discharge jacket 16 against the expansion of the pump housing 9, and thereby closes the heart chamber opposite the blood vessel 1. When the pump is operated it will generate excess pressure and propels blood from the discharge openings 17 in radial and axial direction, which results in the discharge jacket 16 lifting up radially, and the opening of the heart valve 18 with sufficient pressure in order to allow blood into the blood vessel 1 past the proximal expansion of the pump housing 9 via the discharge jacket 16. This is the case particularly in that phase, in which the residual function of the heart being supported by the pump brings about an additional pressure increase in the inflow area of the pump. In this manner it is ensured that the blood flow from the heart chamber into the blood vessel is modulated with the chronological structure of the natural heart function.

Figure 3:
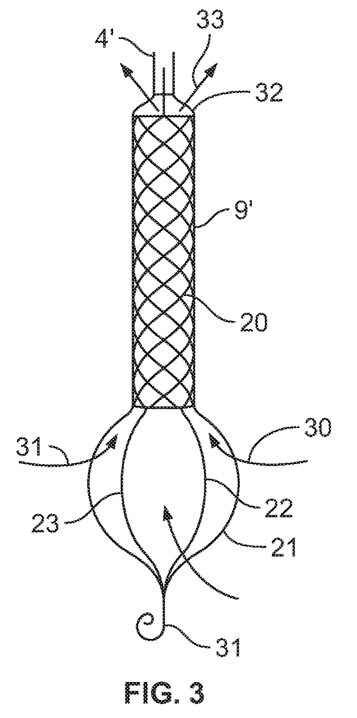

FIG. 3 shows in a side view another blood pump having a pump housing 9', in which the cage-like reinforcement elements 20 are illustrated in the form of wire-like braces. The reinforcement elements 20 are continued at the distal end of the pump housing 9' in free braces 21, 22, 23 into a suction cage, which allows the inflow of blood as indicated by the arrows 30, 31.

The suction cage 21, 22, 23 further has a so-called pigtail 31 at the distal end thereof, which serves to prevent the latching on of the suction cage on a vessel wall.

At the proximal end thereof, the pump housing 9' has an ejection opening 32 at the front, from which the blood, indicated by arrow 33, may be ejected into a blood vessel.

The proximal extension of the pump housing 9' is formed by a catheter 4', which has a hollow space in the interior thereof for accommodating a drive shaft for the pump.

The pump housing 9' is constructed with reinforcement elements 20 such that it may be radially well compressed together with the suction cage.

The reinforcement elements 20 may, for example, be integrated into a pliable film, which forms the housing skin and is not stretchable such that it prevents an expansion of the pump housing 9', after the expansion of the braces 20, beyond a firmly defined state.

Figure 4:
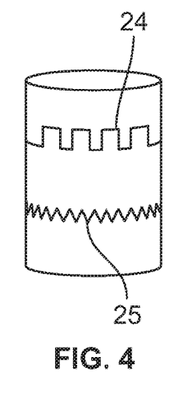

FIG. 4 shows in a side view a cylindrical section of a pump housing with inserted reinforcement elements 24, 25, which, revolving in circumferential direction, are configured in a meandering manner in case of the reinforcement element 24, and in the manner of a saw tooth in case of the reinforcement element 25. This form allows a simple radial expansion and compression of the housing. Additionally, reinforcement elements extending transversely to the same may also be provided.

Figure 5:
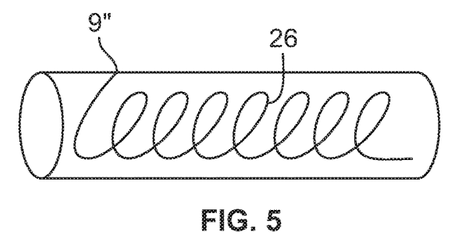

In FIG. 5 a reinforcement element 26 is schematically indicated, which is integrated in a housing 9" as a compression spring. This reinforcement element 26 may also be compressed in a simple manner.

Figure 6:
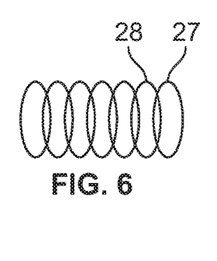

FIG. 6 shows a plurality of circular rings 27, 28, which overall are formed into a tube, and may support a pump house in this manner, which is not illustrated.

Figure 7:
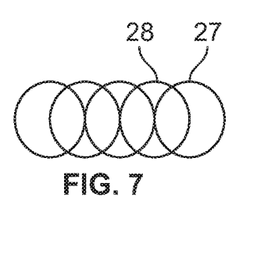

The circular rings may be pivoted against each other about an axis located in the drawing plane such that all are located in the same plane, as illustrated in FIG. 7. In this position the reinforcement elements 27, 28 are very strongly compressed in a radial direction (perpendicular to the drawing plane), while have unchanged measurements in radial direction perpendicular thereto.

Figure 8:
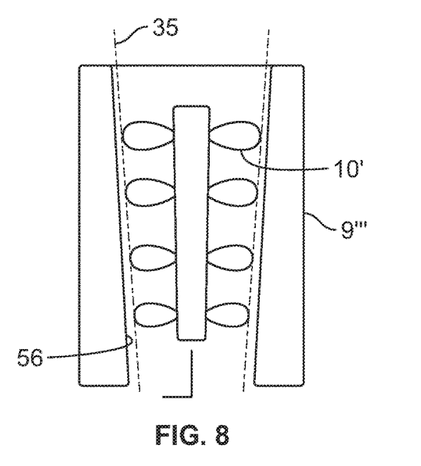

FIG. 8 illustrates a longitudinal section of part of a pump housing with a rotor, wherein the pump housing 9''' has a housing interior tapered conically at an acute angle. The cone angle is exaggerated in the figure to illustrate it better. Cone angles in a magnitude of a few degrees, in particular between 0.5° and 6°, further in particular smaller than 2°, are suitable as the cone angles. The exterior contour 15 of the rotor 10', illustrated as a dotted line, is also embodied in a conical manner, that is to say advantageously with the same cone angle as the interior of the housing 9'''.

If the rotor 10' is pulled into the narrowing area of the cone of the pump housing 9''', for example, by means of the drive shaft (not illustrated), the result is a fit between the exterior contour of the rotor 10' and the interior wall of the housing 9''' that is become increasingly narrower. The rotor may be pulled until the optimum pump gap has been achieved.

Figure 9:
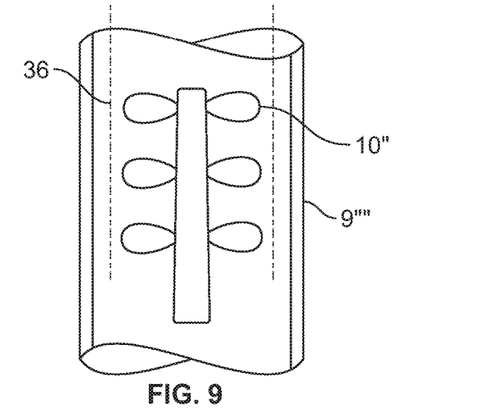

Contrary to FIG. 8, FIG. 9 shows an ideal cylindrical pump housing 9''' with an also cylindrical interior, in which a rotor 10'' is disposed, also having a cylindrical contour indicated by the dotted line 36. This configuration is insensitive to axial displacements of the rotor 10'' opposite of the housing 9''''.

Figure 10:
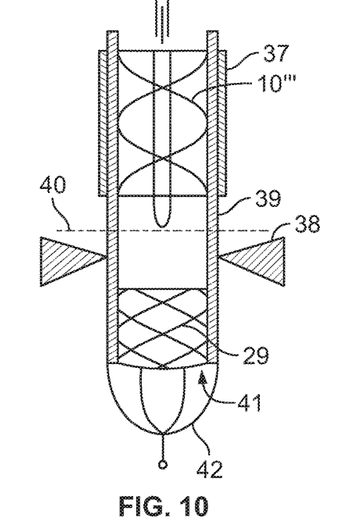

FIG. 10 schematically shows a longitudinal section of a pump housing 39 with a rotor 10'''. The exterior contour of the rotor 10''' is embodied in a cylindrical manner, and it is located in a cylindrical section of the housing 39. Reinforcement elements 29 are integrated into the housing wall of the housing 39 by means of casting, which are responsible for the expansion of the pump, and stretch the housing skin. A stretch-resistant element 37 in the form of an annular strip is illustrated, which radially surrounds the housing skin of the housing 39, thus effectively limiting the radial expansion of the pump housing 39. The reinforcement elements 29 are also still stretched in the expanded state of the pump at such a distance that they will react to any further expansion of the pump housing 39 with a certain excess force. This leads to the fact that a force acting radially from the exterior onto the pump housing 39 and does not exceed a magnitude of between 1 and 25 N, will not result in a radial compression of the housing 39.

The stretch-resistant element 37 may be embodied, for example, as a high-strength plastic film, in particularly also with reinforcement fibers revolving in circumferential direction, e.g. made from or with glass fiber or carbon fiber materials, or also from or with aramide fibers or nylon fibers.

The heart valve of the heart into which the pump is inserted, is indicated in FIG. 10 by the reference number 38. It is also shown that the pump housing 39 axially projects beyond the end of the rotor 10''' in distal direction, illustrated by a dotted line. The pump is positioned in the heart chamber such that the rotor 10''' is located outside of the heart chamber in a blood vessel, while part of the housing 39 projects distally from the dotted line 40 into the heart chamber. In the heart chamber itself the suction opening 41 is disposed, which is covered by a suction cage 42.

The length of the housing extension of the housing 39 distally from the end 40 of the rotor up to the suction opening 41 may be between a few millimeters and several centimeters, such as between 0.5 and 10 cm, in particular between 0.5 and 5 cm, or 0.5 and 2 cm.

Figure 11:
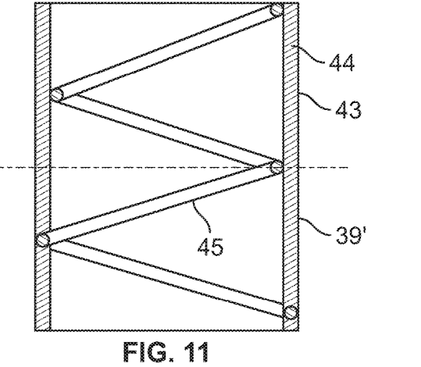

FIG. 11 illustrates another structure of the pump housing 39', in which a housing exterior skin 43 is directly equipped with reinforcement fibers revolving in circumferential direction such that the housing skin 43 itself forms the stretch-resistant element. A helical reinforcement element 45 is illustrated above the horizontal dotted line radially within the housing skin 43, which may be formed by a steel spring coil. However, the coil may also be formed by plastic, and integrally cast into the housing skin, as illustrated below the dotted line.

Figure 12:
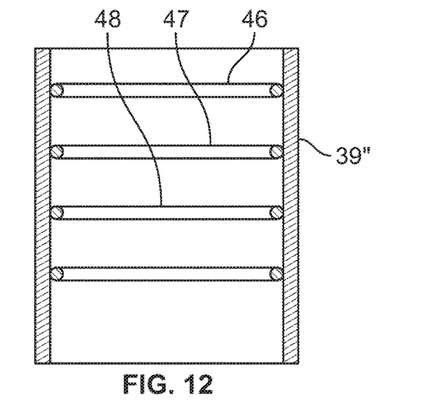

FIG. 12 illustrates a pump housing 39'' consisting of a material that is inherently stretch-resistant, and which surrounds reinforcement elements 46, 47, 48, which are each individually embodied as circular rings. For the purpose of compressing the housing 39'' the individual circular rings may be collapsed at a sufficient force, or pivoted such that all circular rings in the cylindrical axis of the housing 39'' lie on top of each other in the same plane.

Figure 13:
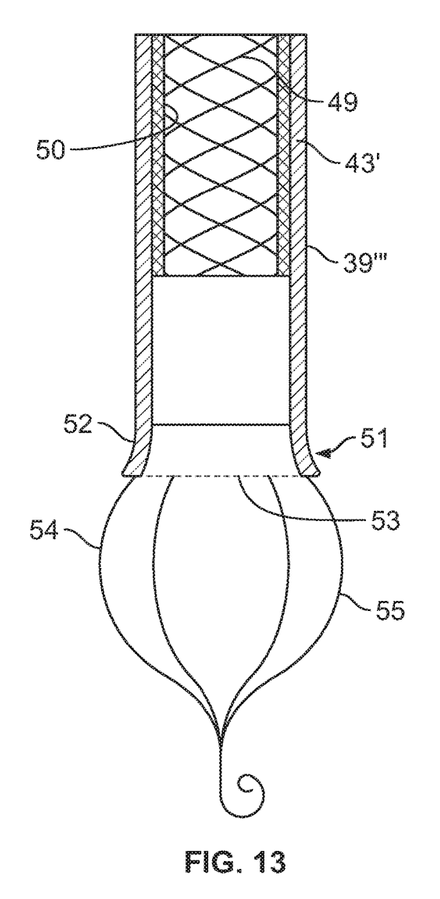

FIG. 13 shows a constellation with a pump housing 39''', wherein the exterior skin 43' of the housing consists of a stretchable membrane, and the reinforcement braces 39 positioned radially on the interior, and forming a structure, which are still elastically compressed for a short distance, even in the expanded state, and act upon further expansion of the housing, are retained by means of a stretch-resistant element 50 in tube form. The stretch-resistant element 50 is cylindrically shaped and has a dimension such that if it is stretched by the reinforcement elements 49, the housing skin 43' is also correspondingly stretched. The elastic excess forces of the reinforcement elements 49 being embodied as a wire structure, have a dimension such that a radial force acting from the exterior onto the housing 39", as long as it does not exceed 3N, will not lead to a deformation of the housing 39", and thus to a reduction of the diameter of the housing interior.

At the distal end 51 thereof, the housing skin 43' has a funnel-shaped extension 52, which facilitates the inflow of blood from the suction opening 53. Simultaneously, in case reinforcement elements are extending in the housing skin 43' of the housing 39''', the same may axially run out from the funnel-type extension 52, and form a balloon-type suction cage. The exemplary reinforcement elements integrated in the wall of the housing 39''', are denoted by 54, 55.

Figure 14:
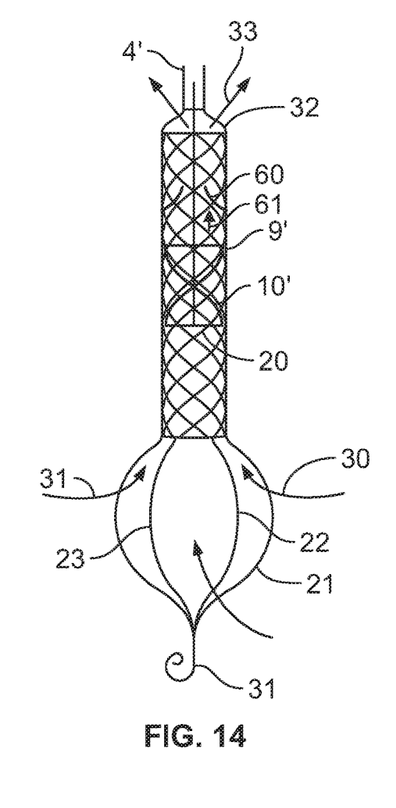

FIG. 14 shows in a side view analogous to FIG. 3 an additional blood pump. Furthermore, the rotor 10' and proximally from the same, an additional valve 60 are illustrated, which prevent the backflow of the blood with the standstill of the pump, thus replacing the valve function in this manner, which is fulfilled in FIG. 2 by the discharge jacket 16 depicted therein, together with the heart valve 18. Here, the valve is embodied by means of multiple baffle-like, advantageously film-like sails, which open in the direction of arrow 61 under the flow pressure of the pump, and close again in case of a standstill of the pump. The sails may be embodied as one piece together with the housing skin, or may be attached to the same. Upon compressing the pump, the sails are also abutted at the wall of the housing, in order to ensure diameter reduction also in this area.

Figure 15:
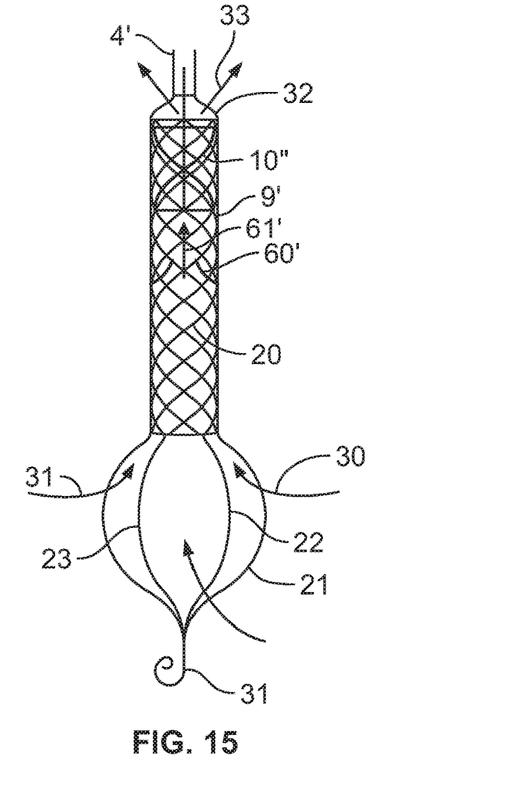

FIG. 15 shows a blood pump analogous to FIG. 14, wherein the arrangement of the rotor and the valve is reversed. This arrangement is advantageous in that the drive shaft of the rotor does not extend within the valve.

Figure 16:
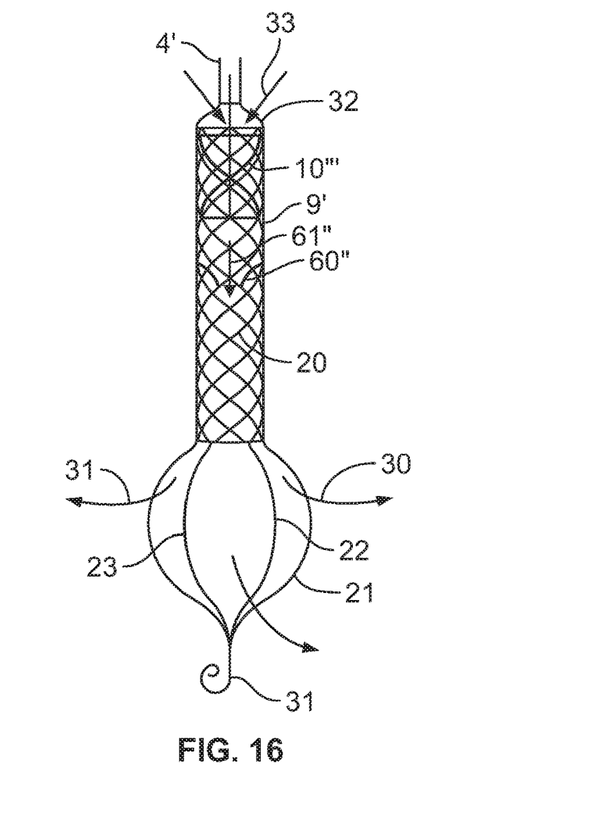

FIG. 16 shows a blood pump analogous to FIG. 15, wherein here, the flow direction of the blood is reversed. Such pumps, in which the blood flows from the proximal end of the housing, at which the catheter is attached, to the distal end of the housing, may be utilized advantageously, for example, for the support of the heart in the right cardiac ventricle.

Figure 17:
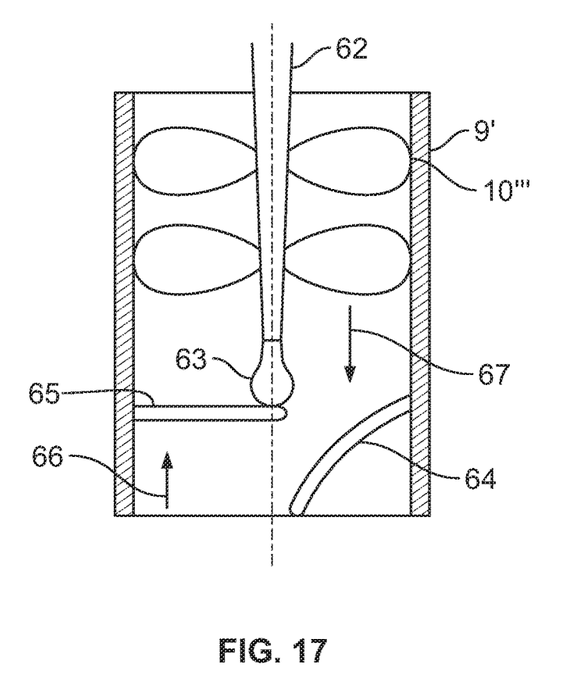
Figure 18:
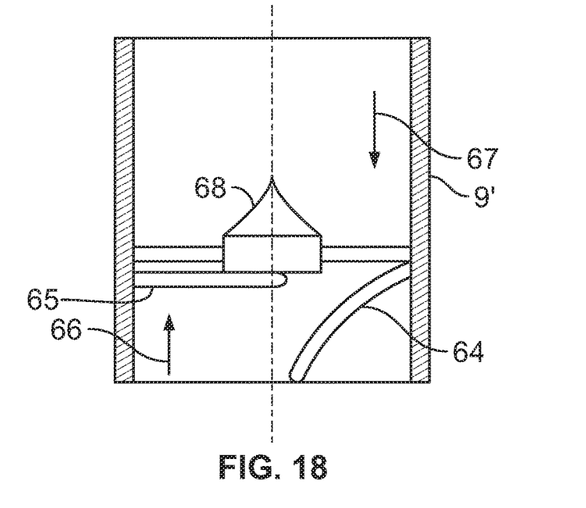

FIG. 17 shows in a longitudinal section, a pump housing 9', as also in FIG. 18. Additionally, a rotor 10''' is illustrated in FIG. 17. As an extension of the shaft 62 a stop body 63 is formed for the sails 64, 65 of a valve, at which the sails engage in case of a flow direction in the direction of arrow 66. In case of a flow direction in the direction of arrow 67, the sails being attached to the housing interior wall open the flow channel/the valve.

FIG. 17 shows a stop body being tapered in the inflow direction.

FIG. 18 shows a stop body having a cone 68 in the inflow direction, however, which is embodied in a flat manner on the discharge flow side thereof.

Aspects of the invention relate to, among others, the following:

1. Blood pump with a pump housing, having a conically tapering housing interior and a rotor disposed in the same, wherein the contour of the rotor is embodied cylindrically, or the exterior contour of which also tapers conically in the same direction, as the interior of the housing, and wherein the cone angles of the exterior contour and of the housing interior are approximately the same.

2. A method for adjusting a blood pump according to a first aspect, wherein the rotor is displaced in the rotation operation axially opposite of the pump housing, until it is ensured by means of determining the load of the drive motor of the pump that the rotor rotates contactless within the pump housing.

3. A pump housing (9, 9', 9", 9''', 9'''', 39, 39', 39", 39''') having an interior for accommodating a pump rotor (10, 10', 10", 10'''), which may be transferred from the radially compressed state into a radially expanded state, wherein at least one element that at an axial distance to the rotor is provided for changing the flow resistance for a fluid flow, in particular a valve, passing through the interior.

4. A pump housing according to aspect 1, wherein the element, in particular the valve, is embodied in the interior of the housing.

5. A pump housing according to one of the previous aspects, wherein the at least one element, in particular the valve, may be transferred from a radially compressed state into a radially expanded state.

6. A pump housing according to one of the previous aspects, wherein the valve function is carried out in the expanded state.

7. A pump housing according to one of the previous aspects, wherein the element has at least one pivoting and/or deformable surface element, in particular in the form of a sail or a baffle, which opens a flow channel under a flow pressure in a first flow direction, and which closes the same upon a standstill of the pump, or with a flow pressure in opposite direction.

8. A pump housing according to one of the previous aspects, wherein the element(s) is/are embodied as film-like sails.

9. A pump housing according to one of the previous aspects, wherein at least one of the elements is attached on the housing.

10. A pump housing according to one of the previous aspects, wherein the element(s) is/are embodied as one piece together with the housing skin.

11. A pump housing according to one of the previous aspects, wherein at least one of the elements may abut on the interior of the housing wall and may be pivoted away from the same.

12. A pump housing according to one of the previous aspects, wherein a fixed body is attached in the interior of the housing, at which the element(s) is/are contact the valve in the closed state.

The invention claimed is:

1. A pump housing having an interior for accommodating a compressible and an expandable pump rotor, the housing comprising;
   a stretch-resistant, radially compressible and expandable housing skin revolving in a circumferential direction, the housing skin formed of a stretch-resistant material which is configured to stretch less than 5% when the housing skin is fully expanded compared to when the housing skin is in an unstressed state, wherein the housing skin limits expansion of the housing;
   at least one reinforcement, the at least one reinforcement being configured to expand in the circumferential direction with expansion of the housing skin; and
   a ring revolving in the circumferential direction of the housing and surrounding the at least one reinforcement at least in sections.

2. The pump housing according to claim 1, further comprising a vault or an arch formed by the at least one reinforcement when the housing is fully expanded, wherein the vault or arch resists forces directed radially toward the interior of at least 1 N without collapsing.

3. The pump housing according to claim 1, wherein the housing skin is formed by a flexible film.

4. The pump housing according to claim 1, wherein the ring is disposed on a radially external side of the housing skin.

5. The pump housing according to claim 1, wherein the ring is disposed on a radially internal side of the housing skin.

6. The pump housing according to claim 1, wherein the at least one reinforcement forms a surface-like, two-dimensional grate, which is bent into the form of a tube.

7. The pump housing according to claim 1, further comprising multiple reinforcements that are (i) pivotable against each other, (ii) form the shape of a tube in a first pivoting state, and (iii) are compressed radially as opposed to the tube shape in a second pivoting state.

8. The pump housing according to claim 1, wherein the at least one reinforcement is comprised of a super-elastic material selected from the group consisting of a super-elastic alloy and nitinol.

9. The pump housing according to claim 1, further comprising a valve within the pump housing at an axial distance to the pump rotor for changing a flow resistance for a fluid flow passing through the interior.

10. The pump housing according to claim 1, wherein the pump housing is for a blood pump.

11. A pump housing having an interior for accommodating a compressible and an expandable pump rotor, the housing comprising;

a stretch-resistant, radially compressible and expandable housing skin revolving in a circumferential direction, the housing skin formed of a stretch-resistant material which is configured to stretch less than 5% when the housing skin is fully expanded compared to when the housing skin is in an unstressed state, wherein the housing skin limits expansion of the housing; and at least one reinforcement, the at least one reinforcement being configured to expand in the circumferential direction with expansion of the housing skin;

wherein the stretch-resistant material comprises stretch-resistant fibers extending in the circumferential direction.

12. The pump housing according to claim 11, wherein the at least one reinforcement exerts elastic forces greater than 1 N radially when the housing is fully expanded.

13. The pump housing according to claim 11, wherein the housing skin is formed by a flexible film.

14. The pump housing according to claim 11, wherein the stretch-resistant fibers are selected from the group consisting of glass fibers, carbon fibers, aramide fibers, and nylon fibers.

15. The pump housing according to claim 11, wherein the at least one reinforcement is comprised of a super-elastic material selected from the group consisting of a super-elastic alloy and nitinol.

16. The pump housing according to claim 11, wherein the housing skin at least sectionally surrounds the at least one reinforcement.

17. The pump housing according to claim 11, further comprising an interior wall limiting the housing interior, the interior wall tapering in an axial direction.

18. The pump housing according to claim 17, wherein the interior wall tapers in a conical manner.

19. The pump housing according to claim 11, wherein the pump housing is for a blood pump.

20. The pump housing according to claim 19, further comprising a catheter attached to the pump housing.

* * * * *

UNITED STATES PATENT AND TRADEMARK OFFICE
CERTIFICATE OF CORRECTION

PATENT NO. : 10,119,550 B2
APPLICATION NO. : 13/261899
DATED : November 6, 2018
INVENTOR(S) : Bredenbreuker et al.

It is certified that error appears in the above-identified patent and that said Letters Patent is hereby corrected as shown below:

In the Specification

Column 1, Line 38, delete "DE 100 59 714 01" and replace with --DE 100 59 714 C1--

Signed and Sealed this
Twenty-fifth Day of June, 2019

Andrei Iancu
*Director of the United States Patent and Trademark Office*